United States Patent [19]

Schwan

[11] 4,042,624
[45] Aug. 16, 1977

[54] ANTIDEPRESSANT 2-[(SUBSTITUTED-1-NAPHTHYLMETHYL)-AMINO]-1-PHENYLPROPANOLS

[75] Inventor: Thomas J. Schwan, Norwich, N.Y.

[73] Assignee: Morton-Norwich Products, Inc., Norwich, N.Y.

[21] Appl. No.: 576,448

[22] Filed: May 12, 1975

[51] Int. Cl.$^2$ .............................................. C07C 91/22
[52] U.S. Cl. .............................. 260/570.6; 260/566 F
[58] Field of Search ...................................... 260/570.6

[56] References Cited

U.S. PATENT DOCUMENTS 3,873,620  3/1975  Pinkas .............................. 260/570.6

FOREIGN PATENT DOCUMENTS 3,564M  9/1965  France .............................. 260/570.6

OTHER PUBLICATIONS

Zikolova et al., "Tr. Nauchno–Izsled. Inst. Firm", 3, pp. 14–19 (1961).

Klosa, "Jour. fur Prakt. Chemie", vol. 36, pp. 1–4 (1967).

Howe et al., "J. Med. Chem.", vol. 11, No. 5, pp. 1000–1008 (1968).

*Primary Examiner*—Robert V. Hines
*Attorney, Agent, or Firm*—Anthony J. Franze

[57] ABSTRACT

Certain 2-[(substituted-1-naphthylmethyl)amino]-1-phenylpropanols of the formula:

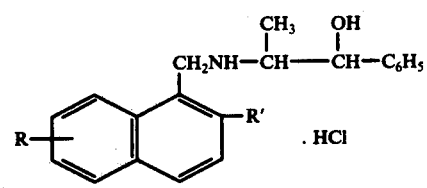

wherein R' is hydrogen or methoxy and R is hydrogen or 5,8-dichloro possess pharmacological activity as antidepressants.

2 Claims, No Drawings

ANTIDEPRESSANT 2-[(SUBSTITUTED-1-NAPHTHYLMETHYL-)AMINO]-1-PHENYLPROPANOLS

This invention relates to chemical compounds. In particular it is concerned with compounds of the formula:

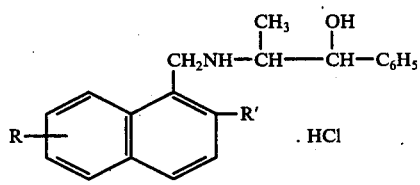

wherein R' is hydrogen or methoxy and R is hydrogen or 5,8-dichloro. These compounds possess pharmacological activity affecting the central nervous system. When administered perorally to animals they exhibit antidepressant action. This antidepressant property is evidenced in the control of tetrabenazine-induced ptosis in mice. An oral dose of 50 mg/kg of these compounds to mice intraperitoneally receiving 35 mg/kg of tetrabenazine counteract the ptosis producing property of tetrabenazine.

The preparation of the compounds of this invention can be accomplished according to the following scheme:

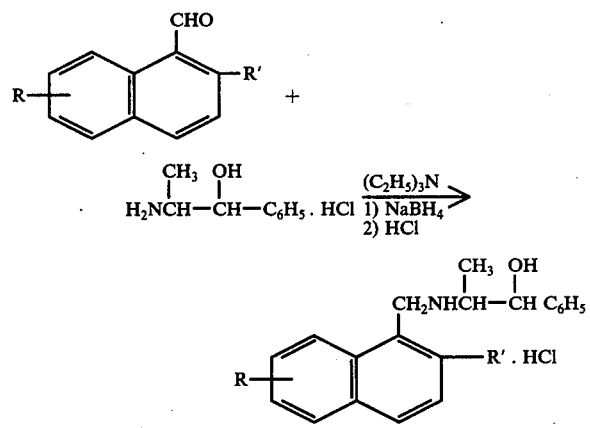

In this scheme R' and R have the significance previously ascribed.

In order that this invention be readily available to and understood by those skilled in the art the following examples are supplied:

EXAMPLE I 2-(1-Naphthylmethylamino)-1-phenyl-1-propanol hydrochloride

A mixture of 78.0 g (0.50 mole) of 1-naphthaldehyde, 50.5 g (0.50 mole) triethylamine, 93.5 g (0.50 mole) of 2-amino-1-phenyl-1-propanol hydrochloride, and 500 ml CH$_3$OH was stirred and refluxed for 45 minutes, then cooled to 15°-20° while 14.0 g (0.38 mole) of sodium borohydride was added over 30 minutes. The reaction mixture was stirred at ambient temperature for 30 minutes, and diluted with 700 ml H$_2$O. The mixture was stirred for 60 minutes and extracted with 600 ml CHCl$_3$ followed by 100 ml CHCl$_3$. The combined organic extracts were washed with 200 ml H$_2$O, dried (MgSO$_4$), and concentrated to dryness in vacuo to give 129 g of the free base of the product.

Treatment of 30.5 g (0.105 mole) sample of the free base dissolved in ethanol with ethanolic hydrogen chloride gave 22.8 g (66%) of the product, m.p. 204°-206°. An analytical sample, m.p. 204°-206°, was obtained by recrystallization from isopropanol.

Anal. Calcd. for C$_{20}$H$_{21}$NO.HCl: C, 73.27; H, 6.77; N, 4.27. Found: C, 72.98; H, 6.79; N, 4.20.

EXAMPLE II 2-(5,8-Dichloro-1-naphthylmethylamino)-1-phenyl-1-propanol hydrochloride A mixture of 28.0 g (0.124 mole) of 5,8-dichloro-1-naphthaldehyde 12.4 g (0.124 mole) triethylamine, 23.2 g (0.124 mole) 2-amino-1-phenyl-1-propanol hydrochloride, and 300 ml CH$_3$OH was stirred and refluxed for one hour, then cooled to 20°-30° while 7.60 g (0.20 mole) of sodium borohydride was added over 15 minutes. The reaction mixture was stirred at ambient temperature for 1¾ hours and diluted with 500 ml H$_2$O. The mixture was extracted with 2 × 200 ml CHCl$_3$. The combined extracts were dried (MgSO$_4$) and concentrated to dryness in vacuo to give 46 g of the free base of the product. Treatment of a 12.0 g (0.033 mole) sample of the free base dissolved in ethanol with ethanolic hydrogen chloride gave 8.3 g (63%) of the product, m.p. 238°-241°. An analytical sample, m.p. 241°-244°, was obtained by recrystallization from absolute ethanol.

Anal. Calcd. for C$_{20}$H$_{19}$Cl$_2$NO: C, 60.54; H, 5.08; N, 3.53. Found: C, 60.43; H, 5.04; N, 3.37.

EXAMPLE III 2-(2-Methoxy-1-naphthylmethylamino)-1-phenyl-1-propanol hydrochloride A mixture of 74.4 g (0.40 mole) 2-methoxy-1-naphthaldehyde, 74.8 g (0.40 mole) 2-amino-1-phenyl-1-propanol hydrochloride, 40 g (0.40 mole) triethylamine, and 500 ml CH$_3$OH was stirred and refluxed for 1.0 hours, then cooled to 10°-20° while sodium borohydride (15.2 g, 0.40 mole) was added over 20 minutes. The reaction mixture was stirred at ambient temperature for 90 minutes and diluted with 500 ml H$_2$O. The mixture was extracted with 2 × 300 ml CHCl$_3$. The combined organic extracts were dried (MgSO$_4$) and concentrated to dryness in vacuo to give 132 g of the free base.

Treatment of a 34.0 g (0.106 mole) sample of the free base dissolved in 200 ml ethanol with 50 ml ethanolic hydrogen chloride gave 26.9 g (79%) of the product, m.p. 208°-210°. The analytical sample, m.p. 208°-210°, was obtained by drying the above product at 61° over NaOH in vacuo.

Anal. Calcd. for C$_{21}$H$_{23}$NO$_2$.HCl: C, 70.48; H, 6.76; N, 3.91. Found: C, 70.78; H, 6.60; H, 3.70.

What is claimed is:

1. The compound 2-(5,8-dichloro-1-naphthylmethylamino)-1-phenyl-1-propanol hydrochloride.
2. The compound 2-(2-methoxy-1-naphthylmethylamino)-1-phenyl-1-propanol hydrochloride.